(12) United States Patent
Squires et al.

(10) Patent No.: US 7,648,505 B2
(45) Date of Patent: *Jan. 19, 2010

(54) GUIDE AND BLADE FOR CONTOURING VERTEBRAL BODIES

(75) Inventors: Craig M. Squires, Memphis, TN (US); Gregory C. Marik, Germantown, TN (US); T. Andrew Simonton, Memphis, TN (US)

(73) Assignee: Warsaw Orthopedic, Inc.

(*) Notice: Subject to any disclaimer, the term of this patent is extended or adjusted under 35 U.S.C. 154(b) by 229 days.

This patent is subject to a terminal disclaimer.

(21) Appl. No.: 11/613,871

(22) Filed: Dec. 20, 2006

(65) Prior Publication Data

US 2007/0123898 A1    May 31, 2007

Related U.S. Application Data

(63) Continuation of application No. 10/174,923, filed on Jun. 19, 2002, now Pat. No. 7,153,303.

(51) Int. Cl.
*A61B 17/14* (2006.01)
*A61B 17/15* (2006.01)

(52) U.S. Cl. .......................................... 606/79; 606/87
(58) Field of Classification Search .................. 606/79, 606/84, 87, 167, 172, 176, 177, 89, 82; 30/304, 30/166.3, 371–373, 392
See application file for complete search history.

(56) References Cited

U.S. PATENT DOCUMENTS 7,153,303 B2 * 12/2006 Squires et al. ................ 606/79

* cited by examiner

*Primary Examiner*—Eduardo C Robert
*Assistant Examiner*—David Comstock

(57) ABSTRACT

A guide and a blade for contouring vertebral bodies. The guide is sized to be mounted between two vertebral members and includes a pair of edges for receiving the blade. The pair of edges are spaced a distance apart for the first edge to align with a first vertebral member, and the second edge to align with a second vertebral member. The blade includes a pair of arms with at least one cutting edge. The arms are sized to fit within the pair of edges respectively. Using the blade and guide comprises inserting the guide adjacent to two vertebral members, and inserting the arms through the pair of edges to contour the ends of the members. In an embodiment with cutting edges at the distal ends of each of the arms, the two vertebral members can be contoured simultaneously.

11 Claims, 7 Drawing Sheets

GUIDE AND BLADE FOR CONTOURING VERTEBRAL BODIES

RELATED APPLICATION

This application is a continuation of U.S. patent application Ser. No. 10/174,923 filed on Jun. 19, 2002 and now issued as U.S. Pat. No. 7,153,303.

BACKGROUND OF THE INVENTION

Current surgical procedures often require a great deal of skill from the surgeon. The procedures may include making fine manipulations by hand using high-speed equipment. One example includes preparing opposing surfaces of vertebral members for receiving an intermediate device, such as preparing the end plates of adjacent vertebrae to receive a graft or interbody fusion device. Each of the end plates is contoured and shaped using a cutting instrument that is held and manipulated by the surgeon. The surgeon guides the cutting instrument by hand and relies upon experience and training to ensure the end plates are contoured correctly.

It may be difficult for the surgeon to determine the amount of contouring and shaping required for each of the vertebral members. A trial-and-error routine is performed as the surgeon removes a first amount of material from one or both surfaces and determines whether the spacing is adequate for receiving the intermediate device. If the spacing is not adequate, the surgeon removes an additional amount from one or both of the surfaces. This routine continues until the proper amount has been removed and the surfaces are adequately prepared. The surgeon is careful not to remove too much from either surface, and instead tends to remove small increments.

SUMMARY OF THE INVENTION

The present invention is directed to a device and method of preparing one or more vertebral members. The device includes a guide having a first edge for alignment relative to the first vertebral member, and a second edge for alignment relative to the second vertebral member. Embodiments of the edges include being part of individual slots within the guide, exposed edges, connected by an opening that extends between a portion of each of the slots, or may be part of a single enlarged opening. A blade is inserted into the first and second edges for contouring the vertebral members. The blade includes a first arm having a first cutting edge on the distal end, and a second arm having a second cutting edge on the distal end. The arms are sized and spaced to correspond to the guides such that both blades are within the guide and contouring the vertebral bodies at the same time.

In some embodiments, the guide may include a spacer that extends outward from a rear face for mounting between the vertebral members. The spacer may include a single prong, or may include a number of prongs depending upon the application.

In one embodiment, the guide is connected to a handle. This allows for the surgeon to position the guide relative to the vertebral members without having their vision obscured by their hands. Additionally, the guide may be too small for the surgeon to hold and the guide provides for more secure gripping. The handle also allows the surgeon to feel the guide during the procedure.

In one embodiment, the blade includes a first arm with a cutting edge, and a second guide arm that does not include a cutting edge. The blade functions by the guide arm contacting the reference edges to position the cutting edge at the proper location relative to the vertebral member.

DETAILED DESCRIPTION

Figure 1:
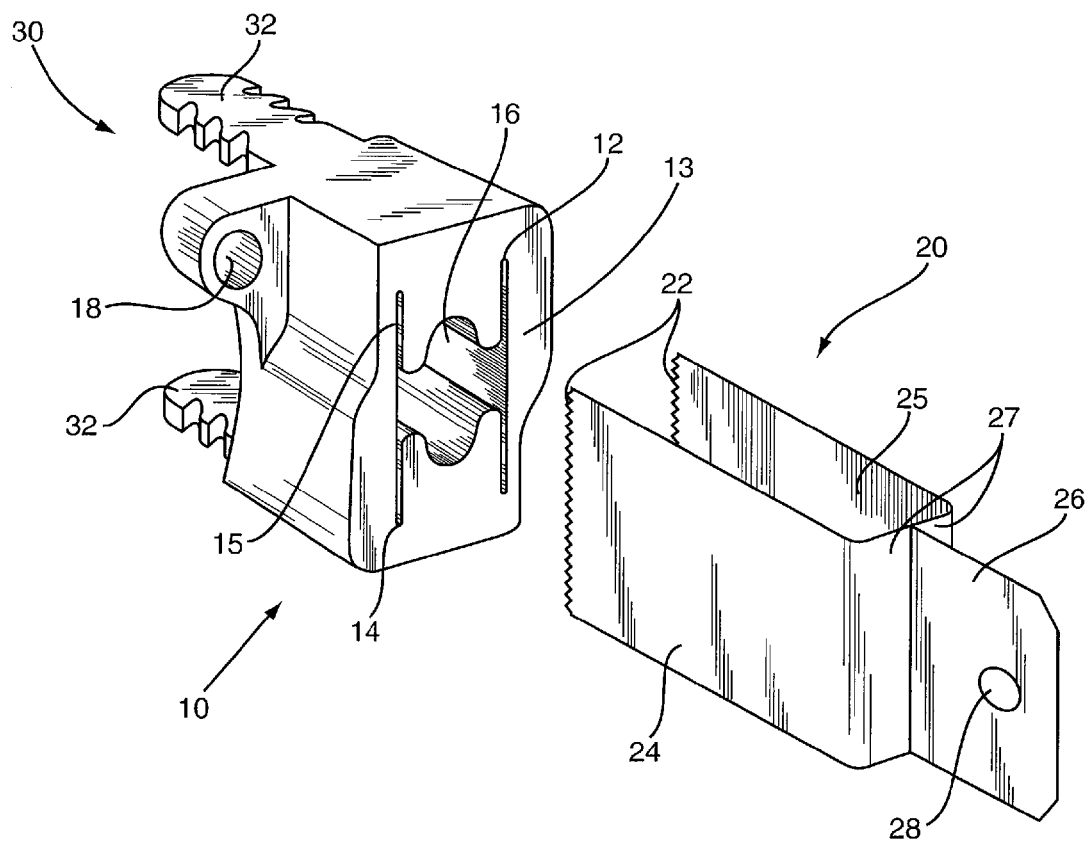
FIG. 1 is a perspective view of a front of a guide and blade constructed according to one embodiment of the present invention.

The present invention is directed to a guide 10 and a blade 20 for contouring vertebral bodies. The guide 10 is sized to be mounted between two vertebral members and has a pair of edges 12, 14 for receiving a blade 20 as illustrated in FIG. 1. The pair of edges 12, 14 are spaced a distance apart for the first edge 12 to align with a first vertebral member, and the second edge 14 to align with a second vertebral member. The blade 20 includes a pair of cutting edges 22 sized to fit within the pair of edges 12, 14 respectively. The cutting edges 22 are positioned at a distal end of a pair of arms 24 with a mount 26 at the proximal end. Using the blade 20 and guide 10 comprises inserting the guide 10 adjacent to two vertebral members, and inserting the blades 20 through the pair of edges 12, 14. The edges 12, 14 are sized for the blades to move within and contour the members.

The guide 10 is constructed of a rigid material, such as stainless steel. The guide 10 is sized such that the first and second edges 12, 14 position the blade at the proper placement relative to the vertebral members and support the blade 20 during the contouring operation. The guide 10 may also act as a spacer to position the two vertebral members an appropriate distance apart for performing the contouring process. In one embodiment, guide 10 is constructed of a unitary member. In another embodiment, guide 10 is an assembled part comprising two or more different sections.

Figure 2:
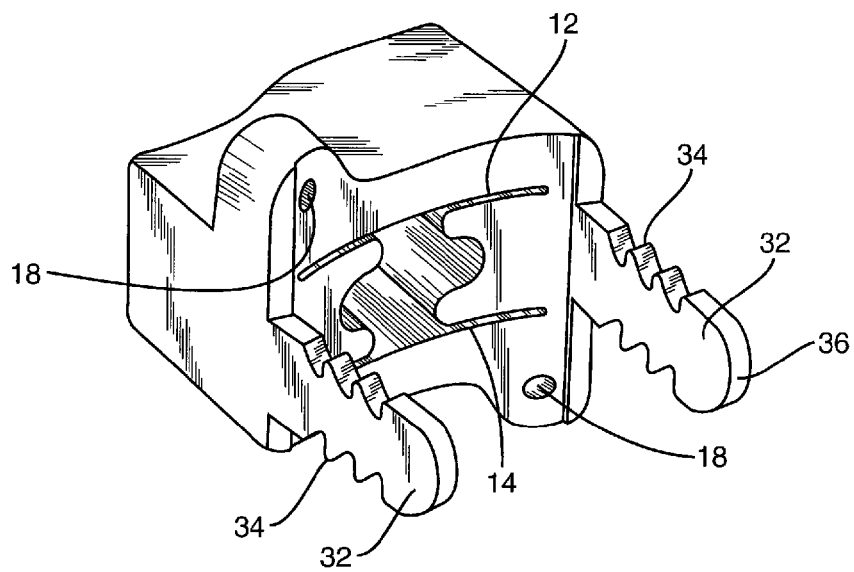
FIG. 2 is a perspective view of the rear of the guide illustrated in FIG. 1.

The first and second edges 12, 14 extend through the guide 10 and position and support the blade 20 while contouring the vertebral members. In the embodiment illustrated in FIGS. 1 and 2, the first and second edges 12, 14 are part of slots 13, 15 respectively, that have a width to receive the blade 20. In this embodiment, the first and second edges 12, 14 may be either the interior or exterior edge of the slots 13, 15. The slots 13, 15 have a length and a width greater than the blade 20 to provide room for the blade 20 to operate during the contouring process. The slots 13, 15 may be sized for the blade 20 to reciprocate back and forth, up and down, or various other cutting techniques that are well known in the art. Slots 13, 15 may have a variety of widths for alignment relative to the vertebral members. The first and second edges 12, 14 may have a variety of shapes depending upon the specific application. In the embodiment illustrated in FIGS. 1 and 2, the first and second edges 12, 14 are parallel to contour parallel ends of the adjacent vertebral members. In the embodiment of FIGS. 1 and 2, the first and second edges 12, 14 are straight. However, depending upon the application, other embodiments may be included such as curved edges and jagged edges. In one embodiment, the blade 20 is shaped to conform to the shape of the edges 12, 14.

In some embodiments, an opening 16 extends between the first and second edges 12, 14. The opening 16 is sized for the surgeon to visually observe the contouring process. The opening 16 further allows for access to the vertebral members for irrigation and bone removal during the contouring process. Opening 16 may have a variety of sizes and shapes depending upon the application. Opening 16 may extend to include the first and second edges 12, 14 as illustrated in FIGS. 1 and 2. In another embodiment, opening 16 is positioned between the first and second edges 12, 14.

In one embodiment such as illustrated in FIGS. 1 and 2, a spacer 30 extends from a rear face of the guide 10 for spacing the vertebral members. Spacer 30 may have a variety of shapes to fit between the vertebral members and space them a predetermined distance apart. Spacer 30 is spaced between the first and second edges 12, 14 to not interfere with access to the vertebral members during the contouring. Worded in another manner, the distance between the first and second edges 12, 14 is about equal to or greater than the width of the spacer 30. In one embodiment, the distance between the first and second edges 12, 14 is about the same as the width of the spacer 30 such that the reference edges 12, 14 align with the edges of the vertebral members to contour only a small amount. In another embodiment, the distance between the first and second edges 12, 14 is greater than the width of the spacers 30 such that reference edges 12, 14 align further on the vertebral members to contour a larger amount.

In one embodiment illustrated in FIGS. 1 and 2, spacer 30 includes two prongs 32 that extend outward from the guide 10. Each prong includes jagged edges 34 to reduce the likelihood of the guide 10 inadvertently moving from between the vertebral members. In this embodiment, the jagged edges are angled from the ends toward the guide body such that insertion of the prongs 32 is not made more difficult or troublesome than with smooth edges. The angled edges 34 catch on the vertebral members to prevent inadvertent removal.

Apertures 18 may be positioned for attaching the guide 10 to the vertebral members. Apertures 18 may be spaced at a variety of locations about the guide 10. In one embodiment illustrated in FIGS. 1 and 2, apertures 18 are located on opposite edges such that a first aperture is aligned with a first vertebral body and a second aperture is aligned with a second vertebral body. Each aperture 18 is sized to receive a fastener 19 for connection to the vertebral members.

In one embodiment, blade 20 comprises first and second arms 24, 25 extending a distance apart by a span 27. A mount 26 is positioned opposite the arms 24, 25 for attachment to a drive source. In one embodiment, arms 24, 25 are the same length such that cutting edges 22 at the distal end are aligned and contour the vertebral members to the same depth. The arms 24, 25 are spaced a distance apart to align respectively with the first and second edges 12, 14. In one embodiment, arms 24, 25 are parallel and span 27 is substantially perpendicular. The height of the blade 20 is the distance extending between the edges 22 and the span 27. During use, the span 27 may contact the front face of the guide 10 to control the depth of contouring of the vertebral members.

In one embodiment, cutting edges 22 include a plurality of individual teeth that contact the vertebral members. In one embodiment, cutting edges 22 are substantially straight. In another embodiment, cutting edges 22 have an arc such that the midsection extends outward from the mount 26 a greater distance than the outer edges. The amount of arc may vary depending upon the application. Other types of cutting edges 22 with different teeth sizes and orientations are known and may be used in the present invention.

Mount 26 provides for attaching the blade 20 to a power device. Mount 26 may have a variety of shapes and sizes, such as a single outwardly extending fin as illustrated in FIG. 1. Apertures 28 may be positioned for attaching the blade 20 to the power device.

Figure 3:
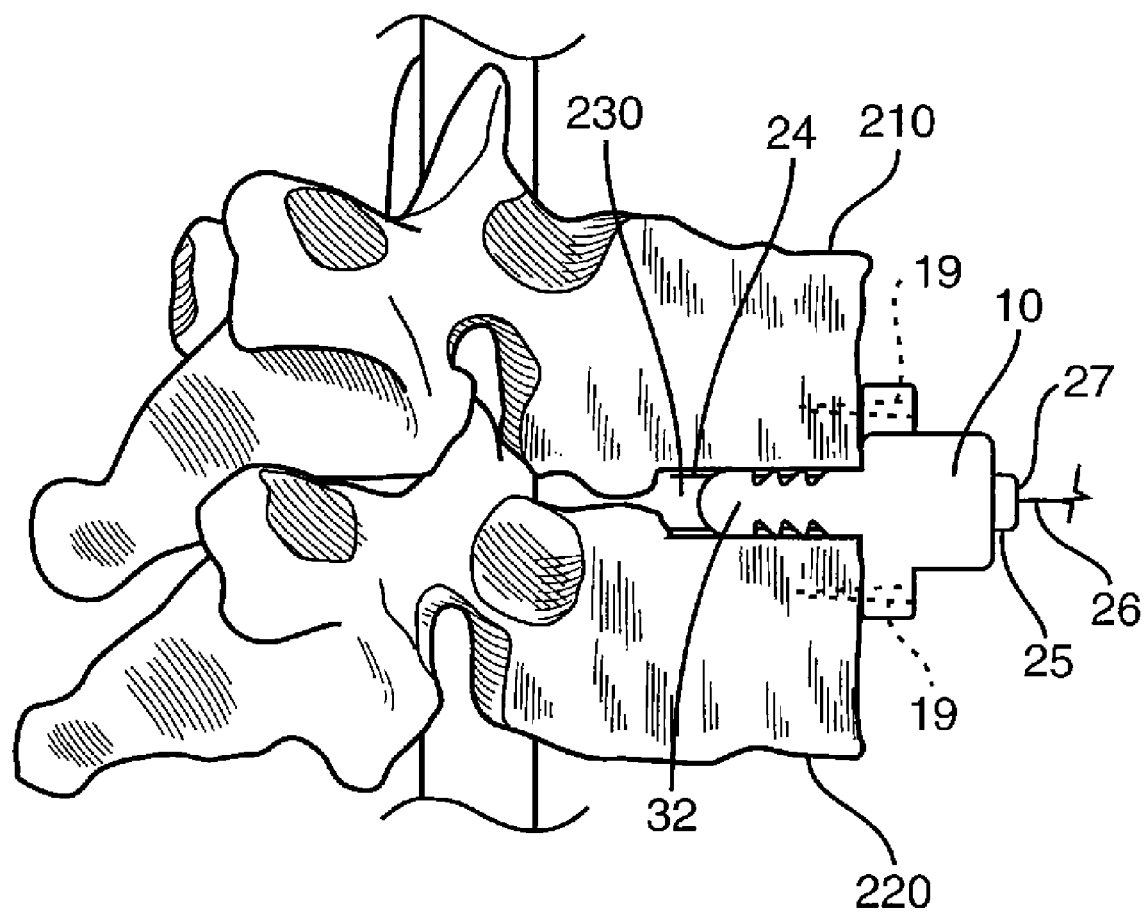
FIG. 3 is side view illustrating the guide and blade relative to two vertebral members according to one embodiment of the present invention.

FIG. 3 illustrates one embodiment of the guide 10 and blade 20 in use. A first vertebral member 210 and a second vertebral member 220 are separated with a disc space 230 positioned therebetween. Guide 10 is attached via fasteners 19 extending through the apertures 18 into the first and second vertebral members 210, 220. Prongs 32 are positioned within the disc space 230 and space apart the first and second vertebral members 210, 220. With the guide 10 attached, the first edge 12 is positioned relative to the first vertebral member 210 and the second edge 14 is positioned relative to the second vertebral member 220. Blade 20 is inserted within the guide 10 with the first arm 24 aligned with the first edge 12 and the second arm 25 aligned with the second edge 14. The blade arms 24, 25 are sized to extend through the guide such that the cutting edges 22 contact the vertebral members 210, 220. In this embodiment, end plates within the vertebral members 210, 220 are contoured. The blade 20 is configured such that both vertebral members 210, 220 are contoured concurrently.

Figure 4:
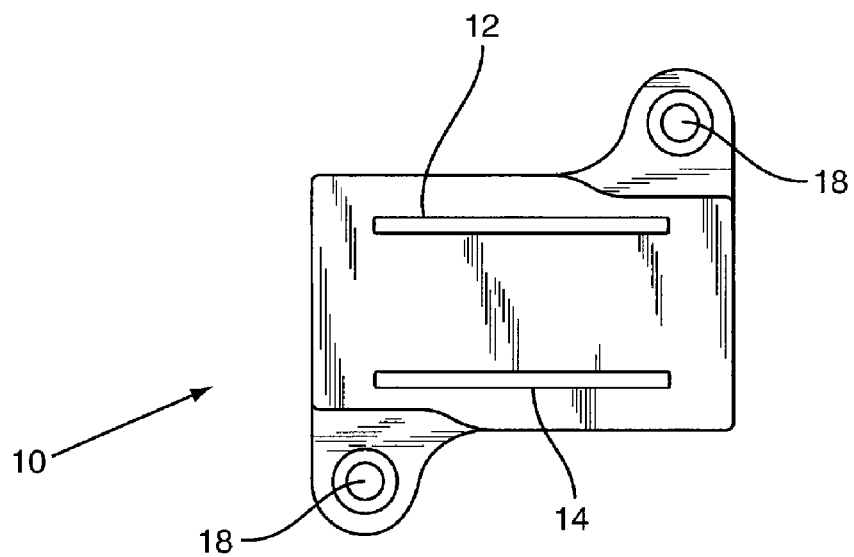
FIG. 4 is a front view of a guide constructed according to another embodiment of the present invention.
Figure 5:
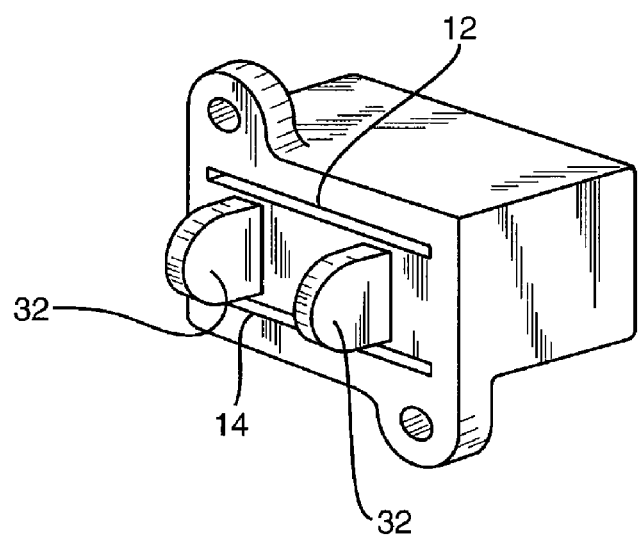
FIG. 5 is a perspective view of a rear of the guide illustrated in FIG. 4.
Figure 6:
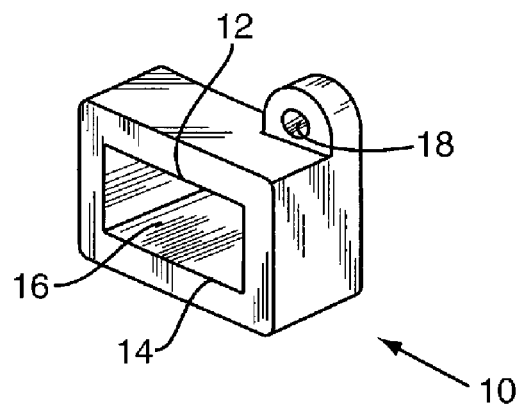
FIG. 6 is a perspective view of a front of a guide constructed according to another embodiment of the present invention.

FIGS. 4 and 5 illustrate another embodiment of the guide 10. The guide 10 includes first and second edges 12, 14 separated a distance apart by a solid guide body. The slots including the first and second edges 12, 14 may have a variety of widths depending upon the application. This embodiment does not include an opening. FIG. 5 illustrates a rear view having a pair of spacers 32 that extend outward from a rear face of the guide 10. The spacers 32 are spaced inward from the edges of the guide 10 at points directly between the first and second edges 12, 14. FIG. 6 illustrates another embodiment with the guide 10 having a single opening 16 that includes the first and second edges 12, 14. The first and second edges 12, 14 are for positioning and supporting the blade 20. The single opening 16 provides for visual assistance and access to the vertebral members during the contouring process.

Figure 7:
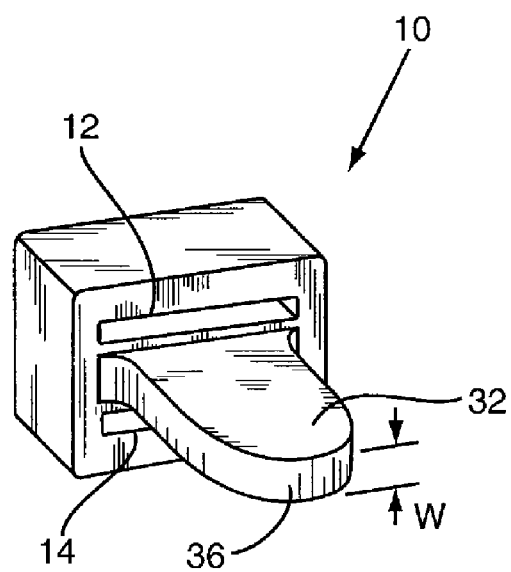
FIG. 7 is a perspective view of the rear of an embodiment of the guide constructed according to another embodiment of the present invention.

FIG. 7 illustrates another embodiment featuring a single spacer 32 extending outward from a rear face of the guide 10. The spacer 32 is positioned between the first and second edges 12, 14. The spacer 32 has a smooth tapered edge that narrows to a rounded end 36. The rounded end 36 eases the insertion between the vertebral members. The spacer 32 is aligned parallel with the first and second edges 12, 14. The spacer 32 has a width w sized to space the vertebral members a distance apart to align the first edge 12 with the first vertebral body and the second edge 14 with the second vertebral body.

Figure 10:
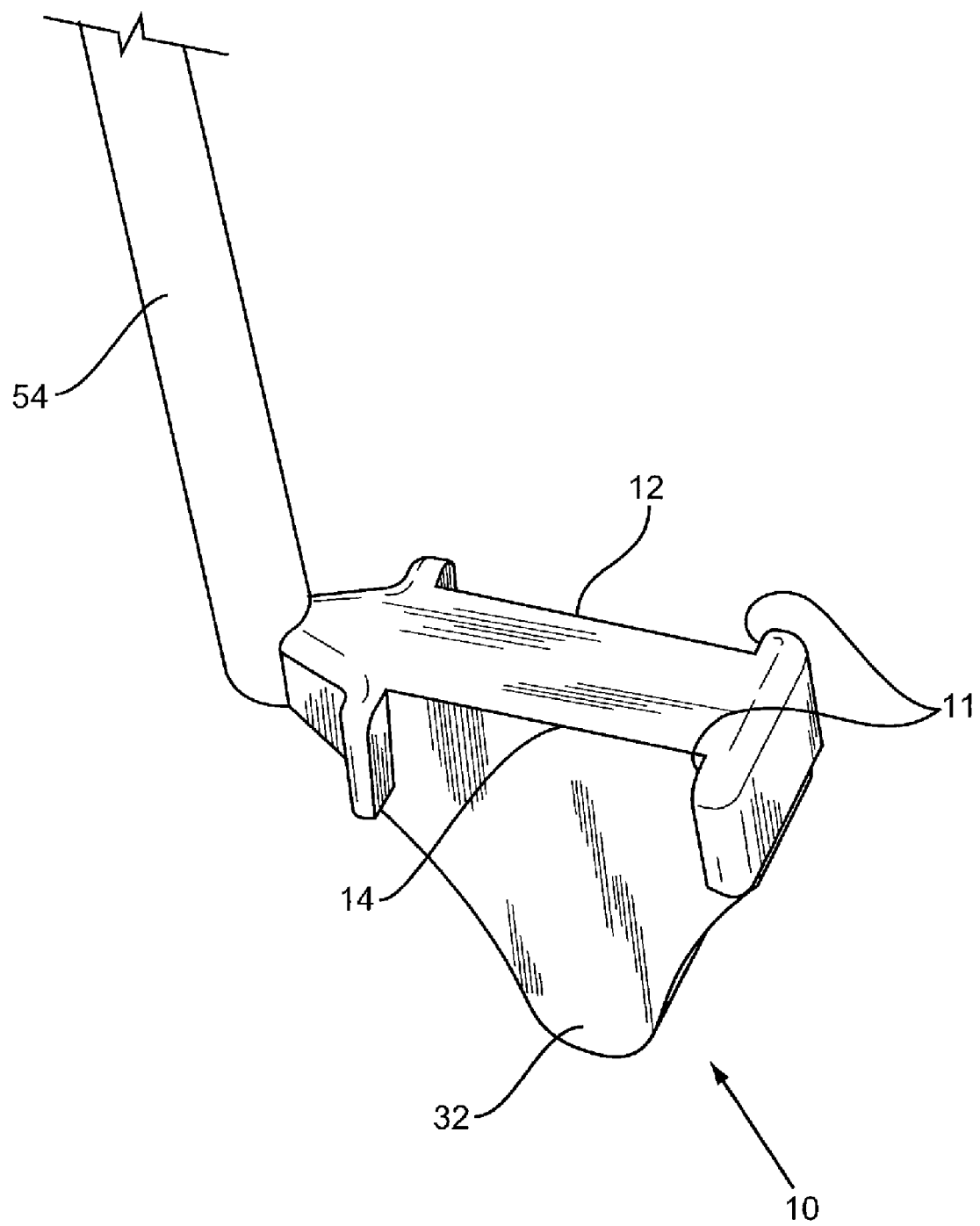
FIG. 10 is a perspective view of another embodiment of a guide constructed according to the present invention.

FIG. 10 illustrates another embodiment of the guide 10 having exposed first and second edges 12, 14. Edges 12, 14 are spaced a desired distance apart to support and guide the blade 20. In one embodiment, stop edges 11 are positioned on one or both ends of the edges 12, 14 to control the extent of blade 20 movement. Stop edges 11 prevent the blade 20 from inadvertently contacting sections of the vertebral members that are not to be contoured. In another embodiment, there are no stop edges 11. Handle 54 may be attached to the guide 10 to position the edges 12, 14. A spacer 32 extends outward from one side of the guide 10. The spacer 32 may have a variety of widths, including a first and second edge that align substantially edges 12, 14, and a width with first and second edges each being positioned within edges 12, 14. In another embodiment (not illustrated), there is no spacer 32.

Figure 9:
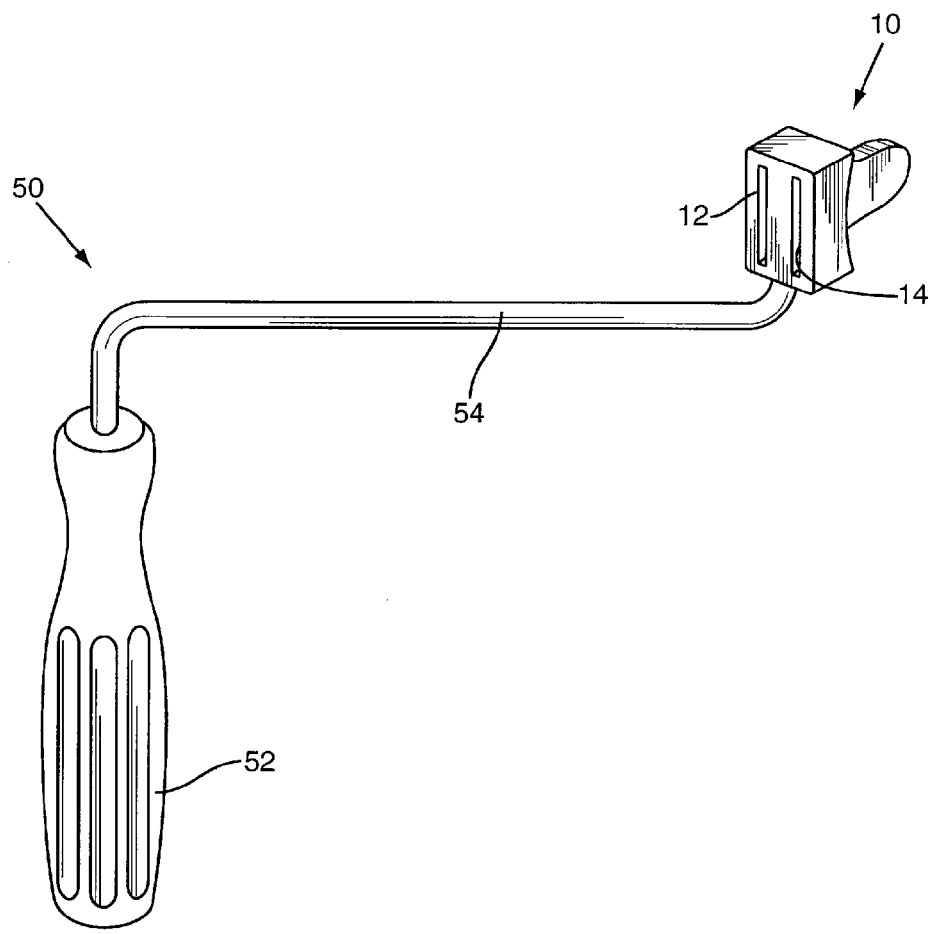
FIG. 9 is a perspective view of a handle attached to a guide in accordance with one embodiment of the present invention.

FIG. 9 illustrates a handle 50 attached to the guide 10. The handle 50 allows the surgeon to position and hold the guide 10 relative to the vertebral members. The handle 50 provides for the surgeon to use tactile senses to position the guide 10. A grip 52 may further assist the surgeon with the feel of the instrument. In one embodiment, grip 52 is off-center from the guide 10 such that the surgeon can visually see the guide 10 when holding the grip 52. The elongated arm 54 may have a variety of sizes and configurations. In one embodiment as illustrated in FIG. 9, a distal end of the elongated arm 54 attaches to a side wall of the guide 10. In one handle embodiment, the guide 10 includes a spacer 30. In another embodiment, the guide 10 does not include a spacer 30. The handle 50 may be attached to a variety of different guides 10.

A variety of different power sources may drive the blade 20. Embodiments include a rechargeable battery, gas turbine mechanism, and any standard electrical source, such as 110 volt, 60 cycle power sources, with or without a transformer to reduce the voltage as necessary. In one embodiment, the blade 20 is oscillated back and forth in a direction parallel with or aligned with the first and second edges 12, 14. In another embodiment, blade 20 is oscillated in an in-and-out direction substantially perpendicular to the first and second edges 12, 14.

Figure 8:
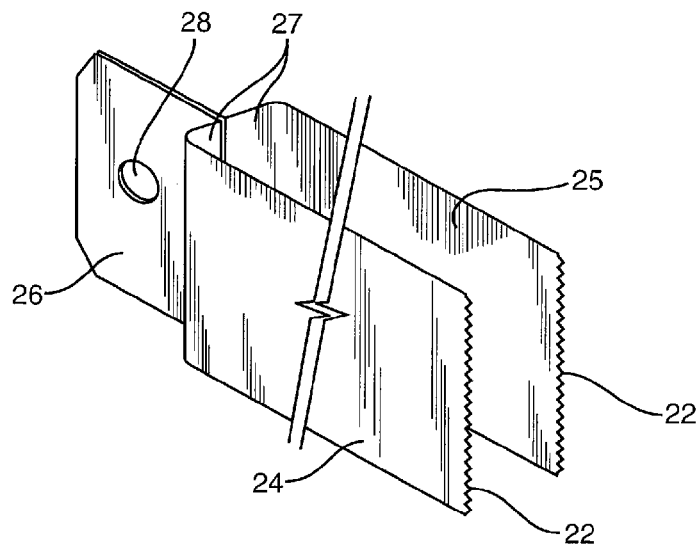
FIG. 8 is a perspective view of the blade constructed according to one embodiment of the present invention.

In one embodiment as illustrated in FIG. 8, blade 20 is constructed of a single piece of material having a fold that comprises the edge of the mount 26. In this embodiment, the arms 24, 25 and span 27 is a single ply, with the mount 26 being a double play. In another embodiment as illustrated in FIG. 1, the mount 26 is a separate piece that is attached to the span 27 and arms 24, 25.

Figure 11:
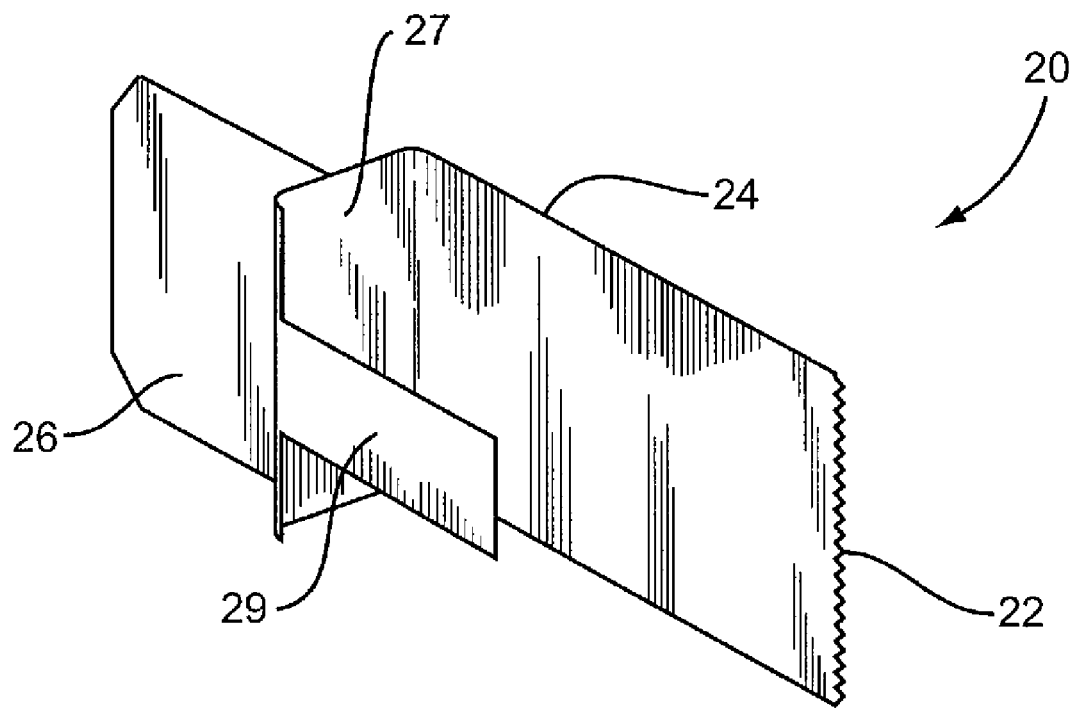
FIG. 11 is a perspective view of another embodiment of the blade constructed according to the present invention.

FIG. 11 illustrates another embodiment of a blade 20. The blade comprises a first arm 24 with cutting edge 22. A second arm comprises a guide arm 29 sized to contact a first or second edge 12, 14 to position the first arm 24. Guide arm 29 does not include a cutting edge 22. The guide arm 29 is sized to contact one of the reference edges 12, 14 and may have a number of different shapes and sizes. The guide arm 29 may have a variety of lengths, provided it is not of such a length to contact the vertebral members and interfere with the contouring process. In the guide of FIG. 10, the span 27 may be wider than the distance between the reference edges 12, 14. The cutting edge 22 of the first arm 24 is aligned by the guide arm 29 contacting one of the reference edges 12 or 14 as the first arm 24 may be spaced from and not contact the other reference edge 12 or 14.

In one embodiment, the first and second arms 24, 25, or the first arm 24 and guide arm 29 are spread apart wider than the distance between the first and second reference edges 12, 14. In this embodiment, the position of the blade performing the contouring is accomplished by the opposite reference edge. By way of example using the guide illustrated in FIG. 10 and the blade illustrated in FIG. 1, the first arm 24 and second arm 25 are spaced apart a distance greater than the distance between the reference edges 12, 14. When the first arm 24 and cutting edge 22 is contouring the vertebral member at a point spaced from the first reference edge 12, the position of the contouring is aligned by the second arm 25 contacting the second reference edge 14. The opposite vertebral member may then be contoured by the second arm 24 at a position aligned by the first arm 24 contacting the first reference edge 12. In the embodiment of the blade illustrated in FIG. 11, cutting edge 22 is first aligned by the guide arm 29 contacting the first reference edge 12, and then contouring the opposite vertebral member by the guide arm 29 contacting the second reference edge 14. This embodiment may be accomplished using an opened sided guide as illustrated in FIG. 10, or a closed sided guide with adequately wide slots such as illustrated in FIG. 1.

In one embodiment of using the guide 10 and blade 20, the guide 10 is positioned relative to the two vertebral members. In one embodiment, the guide 10 is attached to the vertebral members by inserting fasteners through apertures 18 within the guide body and into the members. In another embodiment, the guide 10 is attached to a handle 50 and the surgeon holds the guide 10 in position.

Once the guide 10 is properly positioned, the blade 20 is inserted into the guide 10. In one embodiment, the blade 20 includes two opposing arms 24, 25 that align against a first and second edge 12, 14 respectively that extend through the guide 10. The arms 24, 25 each include cutting edges 22 and the vertebral members are contoured at the same time. In this embodiment, the first and second edges 12, 14 locate and support the arms 24, 25 to ensure the proper location and amount of contouring is performed. The edges 12, 14 are sized to allow the blade 10 to move to contour the members. Movement may be oscillating, reciprocating, vibratory, and other known manners. In another embodiment, a first arm 24 contacts a first edge 12 to position a cutting edge 22 on the second arm 25 to contour a first vertebral body. The blade 20 is then re-adjusted with the first arm contacting the second edge to position the cutting edge 22 on the second arm 25 to contour the second vertebral body. Various other manners of orientating and using the guide 10 and blade 20 are disclosed, as these embodiments are merely examples to illustrate several manners of using the invention.

The present invention may be carried out in other specific ways than those herein set forth without departing from the scope and essential characteristics of the invention. The present invention may be used for other applications such as for knee surgery, elbow surgery, and others. In one embodiment, the process of contouring the vertebral members comprises using a plurality of different blades 20 each having increasingly longer arms 24, 25. The vertebral members may already be distracted by other means prior to the application of the guide and blade. The blades are inserted into the guide in order to increase the depth of the contouring until the correct amount has been obtained. In another embodiment, no spacer 30 is positioned on the rear face of the guide 10. The present embodiments are, therefore, to be considered in all respects as illustrative and not restrictive, and all changes coming within the meaning and equivalency range of the appended claims are intended to be embraced therein.

What is claimed is:

1. A device for contouring a first vertebral member and a second vertebral member, comprising:
   a guide comprising a back surface positioned adjacent to at least one of the first and second vertebral members and a front surface positioned opposite the back surface, the guide including a first slot and a second slot each extending through the guide from the front surface to the back surface, each of the first and second slots including a height defined between the front and back surfaces and a length, the guide further including an opening positioned between the first and second slots and extending from the front surface through the guide to the back surface;

a pair of spacers extending outward from the back surface of the guide to space apart the first and second vertebral members; and a blade comprising a pair of arms spaced apart to align the arms with the first and second slots, each arm including a height greater than the height of the first and second slots and a length less than the length of the first and second slots, and including a plurality of cutting teeth on a first end of each arm, and the arms separated by a gap along the height and length of the arms;

the arms of the blade positionable within the first and second slots and extending through the guide and outward from the back surface, the arms sized for non-rotating oscillating movement within the first and second slots, and the vertebral members visible through the opening when the blades are positioned within the first and second slots.

2. The device of claim 1, wherein the first and second slots are spaced a predetermined distance apart with the first slot positioned adjacent to the first vertebral member and the second slot positioned adjacent to the second vertebral member.

3. The device of claim 1, wherein the first and second slots have the same length.

4. The device of claim 1, wherein the spacers are positioned between the first and second slots.

5. The device of claim 4, wherein the spacers are positioned directly between the first and second slots.

6. The device of claim 1, wherein each spacer includes a first surface to contact the first vertebral member and a second surface to contact the second vertebral member, the first and second surfaces oriented essentially parallel to the first and second slots.

7. The device of claim 1, further comprising apertures sized to receive fasteners to mount the guide to the first and second vertebral members.

8. The device of claim 1, wherein the first and second slots are parallel.

9. A device for contouring a first vertebral member and a second vertebral member, comprising:

a guide comprising a back surface positioned adjacent to the first and second vertebral members and a front surface positioned away from the first and second vertebral members, the front surface being substantially flat and the back surface being an elongated curve shape to fit between and space apart the first and second vertebral members, and a pair of parallel guide surfaces each forming an outer surface of the guide, the guide surfaces spaced a predetermined distance apart and extending between the front and back surfaces; and a blade comprising a first arm and a second arm, each of the first and second arms including a first end and a second end, the first and second arms spaced apart at least the predetermined distance, a height of the first arm greater than a height of the guide, and a plurality of cutting teeth on a first end of the first arm, the first and second arms separated by a gap along the height of the first and second arms;

the first and second arms positionable adjacent to the guide surfaces with the first arm extending beyond the back surface of the guide and in contact with the first vertebral member, the first and second arms being sized for non-rotating oscillating movement when positioned adjacent to the guide surfaces.

10. The device of claim 9, wherein the guide further comprises stop edges positioned on one or both lateral edges of the guide surfaces, the stop edges extending beyond the guide surfaces to limit lateral movement of the first and second arms.

11. The device of claim 9, wherein the first arm includes a height greater than the second arm.

* * * * *

UNITED STATES PATENT AND TRADEMARK OFFICE
CERTIFICATE OF CORRECTION

PATENT NO. : 7,648,505 B2
APPLICATION NO. : 11/613871
DATED : January 19, 2010
INVENTOR(S) : Squires et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this

Twenty-third Day of November, 2010

David J. Kappos
*Director of the United States Patent and Trademark Office*